US012586675B2

(12) United States Patent
Kanan et al.

(10) Patent No.: US 12,586,675 B2
(45) Date of Patent: Mar. 24, 2026

(54) SYSTEMS AND METHODS FOR PROCESSING IMAGES FOR IMAGE MATCHING

(71) Applicant: PAIGE.AI, Inc., New York, NY (US)

(72) Inventors: Christopher Kanan, Pittsford, NY (US); Leo Grady, Darien, CT (US)

(73) Assignee: Paige.AI, Inc., New York, NY (US)

( * ) Notice: Subject to any disclaimer, the term of this patent is extended or adjusted under 35 U.S.C. 154(b) by 940 days.

(21) Appl. No.: 17/830,973

(22) Filed: Jun. 2, 2022

(65) Prior Publication Data

US 2023/0022030 A1     Jan. 26, 2023

Related U.S. Application Data

(60) Provisional application No. 63/225,373, filed on Jul. 23, 2021.

(51) Int. Cl.
| | |
|---|---|
| *G16H 30/20* | (2018.01) |
| *G06N 20/00* | (2019.01) |
| *G06V 10/74* | (2022.01) |

(52) U.S. Cl.
CPC ............. *G16H 30/20* (2018.01); *G06N 20/00* (2019.01); *G06V 10/74* (2022.01)

(58) Field of Classification Search
CPC ...................................................... G16H 30/20
USPC ......................................................... 706/12
See application file for complete search history.

(56) References Cited

U.S. PATENT DOCUMENTS

| | | | | |
|---|---|---|---|---|
| 10,790,056 B1 * | 9/2020 | Accomazzi | ......... | H04L 67/1097 |
| 2020/0258223 A1 * | 8/2020 | Yip | ......................... | G06F 18/21 |
| 2020/0364587 A1 | 11/2020 | Kapur et al. | | |

FOREIGN PATENT DOCUMENTS

| | | | | | |
|---|---|---|---|---|---|
| WO | WO-2022221712 A1 * | 10/2022 | | ............. | G16H 30/20 |
| WO | WO-2022226284 A1 * | 10/2022 | | ............. | G06T 5/70 |
| WO | WO-2022235481 A1 * | 11/2022 | | ........... | E21B 47/095 |

OTHER PUBLICATIONS

Emest, Guy. "Combining Deep Learning Networks (GAN and Siamese) to Generate High-Quality, Life-Like Images." AWS Machine Learning Blog, Amazon, Sep. 11, 2017, https://aws.amazon.com/blogs/machine-learning/combining-deep-learning-networks-gan-and-siamese-to-generate-high-quality-life-like-images/.

(Continued)

*Primary Examiner* — Ruay Ho
(74) *Attorney, Agent, or Firm* — Bookoff McAndrews, PLLC

(57) ABSTRACT

A computer-implemented method for processing electronic medical images, the method including receiving a plurality of electronic medical images of a medical specimen associated with a single patient. The plurality of electronic medical images may be inputted into to a trained machine learning system, the trained machine learning system being trained to compare each of the plurality of electronic medical images to each other to determine whether each pair of the electronic medical images matches within a predetermined similarity threshold. The trained machine learning system may output whether each pair of the electronic medical images matches within a predetermined similarity threshold. The output may be stored.

18 Claims, 12 Drawing Sheets

(56)                                    References Cited

OTHER PUBLICATIONS

Choudhary, Anirudh Achoudhary46@Gatech Edu et al., "Learning to Evaluate Color Similarity for Histopathology Images using Triplet Networks", Proceedings of The 2020 Chi Conference on Human Factors in Computing Systems, ACMPUB27, New York, NY, USA, Sep. 4, 2019 (Sep. 4, 2019), pp. 466-474, XP058547389, DOI: 10.1145/3307339.3342170 ISBN: 978-1-4503-6708-0.

Shojogh, Benyamin et al., "Fisher Discriminant Triplet and Contrastive Losses for Training Siamese Networks", 2020 International Joint Conference on Neural Networks (IJCNN), [Online] Jul. 24, 2020 (Jul. 24, 2020), pp. 1-7, XP055865927, DOI: 10;1109/ IJCNN48605.2020.9206833 ISBN: 978-1-7281-6926-2 Internet Retrieved from the Internet: URL:https://ieeexplore.ieee.org/ stampPDF/g etPDF.jsp?tp=&arnumber=9206833&ref=aHR0CHM 6Ly9pZWV1eHBsb3JlLmllZWUub3JnL2Fic3RyYWNOL2RvYtZ W50LzkyMDY4MzM/Y2FzYV90b2lbjlqZ2xDVUUxMUImd0FB QUFBOnJLUHVmRk81UU55ZTNITSlzakVESkdGcVhhQTUOTn pseFhEN21pMFk5eWVPRWxqeHQldWIHVGx4QmQ5TGRFZnJ hSHUwZG04> [retrieved on Aug. 30, 2022] the whole document.

Lin, Zhihuang et al., "Patient Similarity via Joint Embeddings of Medical Knowledge Graph and Medical Entity Descriptions", IEEE Access, IEEE, USA, vol. 8, Aug. 25, 2020 (Aug. 25, 2020), pp. 156663-156676, XP011807308, DOI: 10.1109/ACCESS.2020. 3019577 [retrieved on Sep. 3, 2020].

Yang, Pengshuai et al., "A deep metric learning approach for histopathological image retrieval", Methods, Academic Press, NL, vol. 179, May 19, 2020 (May 19, 2020), pp. 14-25, XP086236831, ISSN: 1046-2023, DOI: 10.1016/J.YMETH.2020.05.015 [retrieved on May 19, 2020].

* cited by examiner

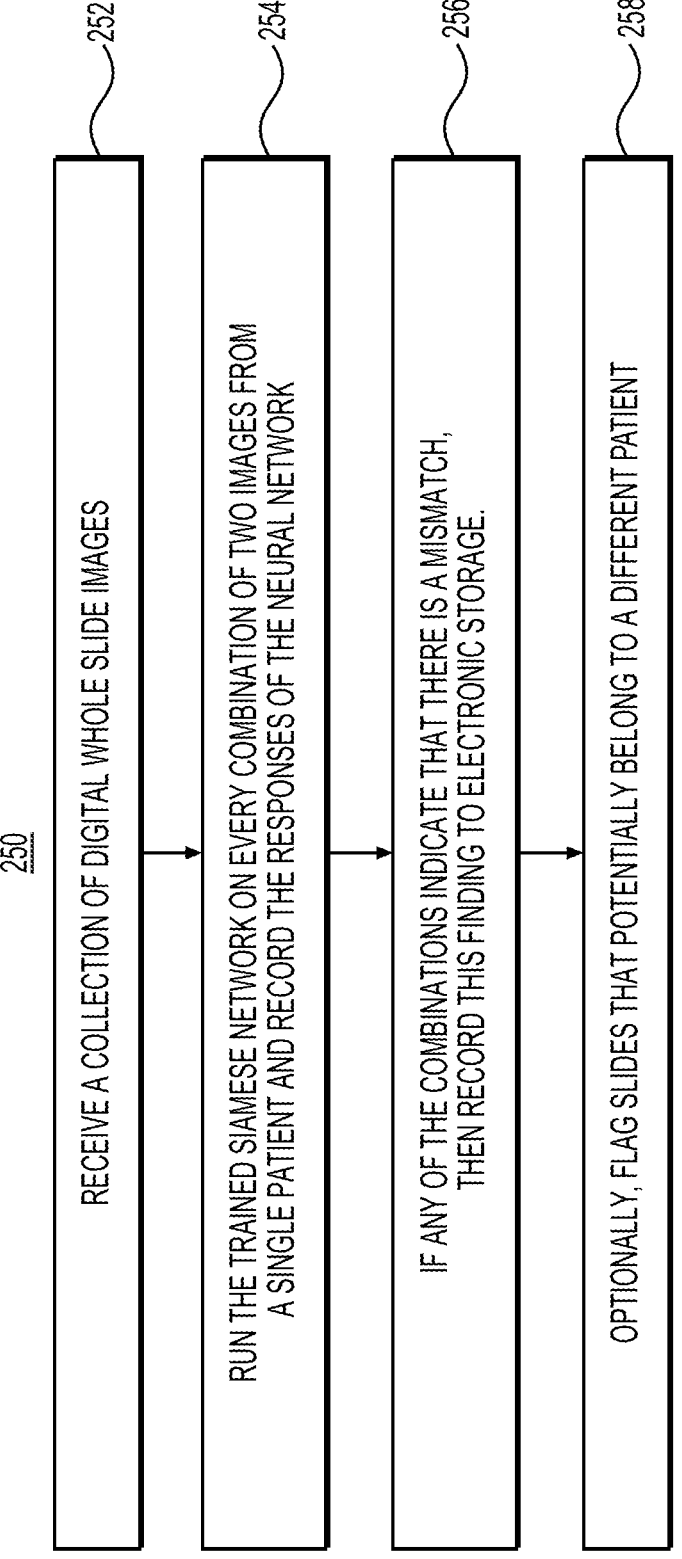

250

252 — RECEIVE A COLLECTION OF DIGITAL WHOLE SLIDE IMAGES

254 — RUN THE TRAINED SIAMESE NETWORK ON EVERY COMBINATION OF TWO IMAGES FROM A SINGLE PATIENT AND RECORD THE RESPONSES OF THE NEURAL NETWORK

256 — IF ANY OF THE COMBINATIONS INDICATE THAT THERE IS A MISMATCH, THEN RECORD THIS FINDING TO ELECTRONIC STORAGE.

258 — OPTIONALLY, FLAG SLIDES THAT POTENTIALLY BELONG TO A DIFFERENT PATIENT

402 RECEIVE A COLLECTION OF DIGITAL WHOLE SLIDE IMAGES FROM ONE OR MORE PATIENTS

404 GENERATE A SET OF MATCHES

406 EXTRACT EMBEDDINGS UTILIZING A PRE-TRAINED NEURAL NETWORK

408 TRAIN A MACHINE LEARNING SYSTEM

410 SAVE THE LEARNED PARAMETERS

450

452 RECEIVE A COLLECTION OF DIGITAL WHOLE SLIDE IMAGES

454 EXTRACT EMBEDDINGS UTILIZING A PRE-TRAINED NEURAL NETWORK

456 RUN THE TRAINED MACHINE LEARNING SYSTEM ON ALL PAIRWISE COMBINATIONS OF EMBEDDING

458 RECORD ANY COMBINATION MISMATCHES

460 OPTIONALLY, FLAG SLIDES THAT POTENTIALLY BELONG TO A DIFFERENT PATIENT

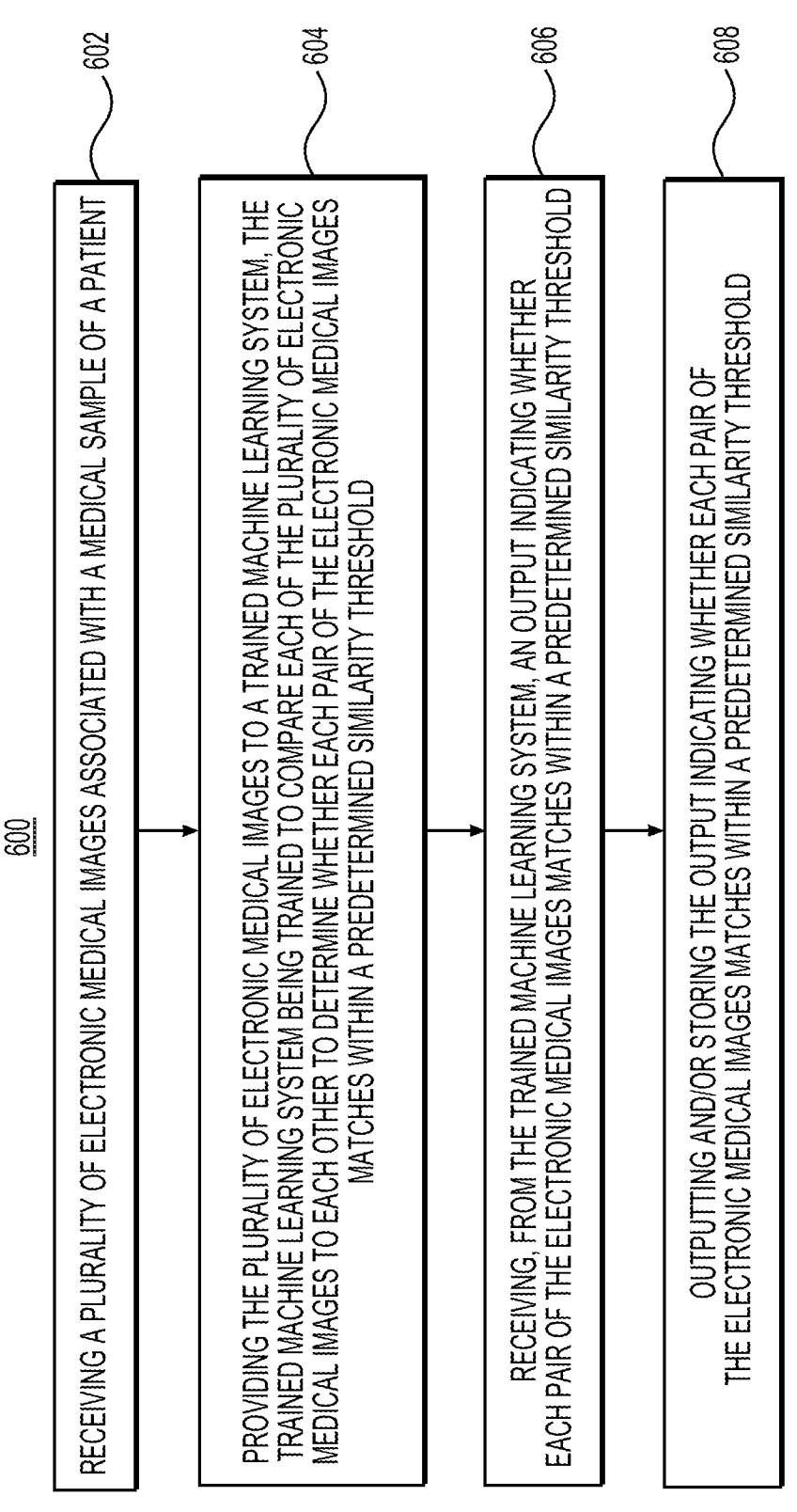

600

602 — RECEIVING A PLURALITY OF ELECTRONIC MEDICAL IMAGES ASSOCIATED WITH A MEDICAL SAMPLE OF A PATIENT

604 — PROVIDING THE PLURALITY OF ELECTRONIC MEDICAL IMAGES TO A TRAINED MACHINE LEARNING SYSTEM, THE TRAINED MACHINE LEARNING SYSTEM BEING TRAINED TO COMPARE EACH OF THE PLURALITY OF ELECTRONIC MEDICAL IMAGES TO EACH OTHER TO DETERMINE WHETHER EACH PAIR OF THE ELECTRONIC MEDICAL IMAGES MATCHES WITHIN A PREDETERMINED SIMILARITY THRESHOLD

606 — RECEIVING, FROM THE TRAINED MACHINE LEARNING SYSTEM, AN OUTPUT INDICATING WHETHER EACH PAIR OF THE ELECTRONIC MEDICAL IMAGES MATCHES WITHIN A PREDETERMINED SIMILARITY THRESHOLD

608 — OUTPUTTING AND/OR STORING THE OUTPUT INDICATING WHETHER EACH PAIR OF THE ELECTRONIC MEDICAL IMAGES MATCHES WITHIN A PREDETERMINED SIMILARITY THRESHOLD

*FIG. 6*

SYSTEMS AND METHODS FOR PROCESSING IMAGES FOR IMAGE MATCHING

RELATED APPLICATION(S)

This application claims priority to U.S. Provisional Application No. 63/225,373 filed Jul. 23, 2021, the entire disclosure of which is hereby incorporated herein by reference in its entirety.

FIELD OF THE DISCLOSURE

Various embodiments of the present disclosure pertain generally to computational pathology workflows for processing electronic images. More specifically, particular embodiments of the present disclosure relate to systems and methods for determining whether digital images of pathology slides match (e.g., correspond to the same individual) within a predetermined similarity threshold.

BACKGROUND

Within the field of computational pathology, having error-free data may be critical for pathologist to perform accurate diagnoses. Errors may occur to pathology data in a number of ways. One of the most consequential errors that may occur is when pathology slides are incorrectly associated with the wrong patient. If physical specimens or digital images of slides are incorrectly assigned to a patient, incorrect diagnoses may occur. A mismatch of slides may occur due to mistakes during scanning, mistakes in the laboratory information system, or mistakes in other areas.

The foregoing general description and the following detailed description are exemplary and explanatory only and are not restrictive of the disclosure. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic medical images, comprising: receiving a plurality of electronic medical images associated with a medical sample of a patient; providing the plurality of electronic medical images to a trained machine learning system, the trained machine learning system being trained to compare each of the plurality of electronic medical images to each other to determine whether each pair of the electronic medical images matches within a predetermined similarity threshold; receiving, from the trained machine learning system, an output indicating whether each pair of the electronic medical images matches within a predetermined similarity threshold; and outputting and/or storing the output indicating whether each pair of the electronic medical images matches within a predetermined similarity threshold.

A system for processing electronic digital medical images, the system including: at least one memory storing instructions; and at least one processor configured to execute the instructions to perform operations including: receiving a plurality of electronic medical images associated with a medical sample of a patient; providing the plurality of electronic medical images to a trained machine learning system, the trained machine learning system being trained to compare each of the plurality of electronic medical images to each other to determine whether each pair of the electronic medical images matches within a predetermined similarity threshold; receiving, from the trained machine learning system, an output indicating whether each pair of the electronic medical images matches within a predetermined similarity threshold; and outputting and/or storing the output indicating whether each pair of the electronic medical images matches within a predetermined similarity threshold.

A non-transitory computer-readable medium storing instructions that, when executed by a processor, perform operations processing electronic digital medical images, the operations including: receiving a plurality of electronic medical images associated with a medical sample of a patient; providing the plurality of electronic medical images to a trained machine learning system, the trained machine learning system being trained to compare each of the plurality of electronic medical images to each other to determine whether each pair of the electronic medical images matches within a predetermined similarity threshold; receiving, from the trained machine learning system, an output indicating whether each pair of the electronic medical images matches within a predetermined similarity threshold; and outputting and/or storing the output indicating whether each pair of the electronic medical images matches within a predetermined similarity threshold.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 2B is a flowchart illustrating methods for how to process an image (e.g., image matching), according to one or more exemplary embodiments herein.

FIG. 6 is a flowchart illustrating methods for how to process an image (e.g., image matching), according to one or more exemplary embodiments herein.

DESCRIPTION OF THE EMBODIMENTS

Figure 1A:
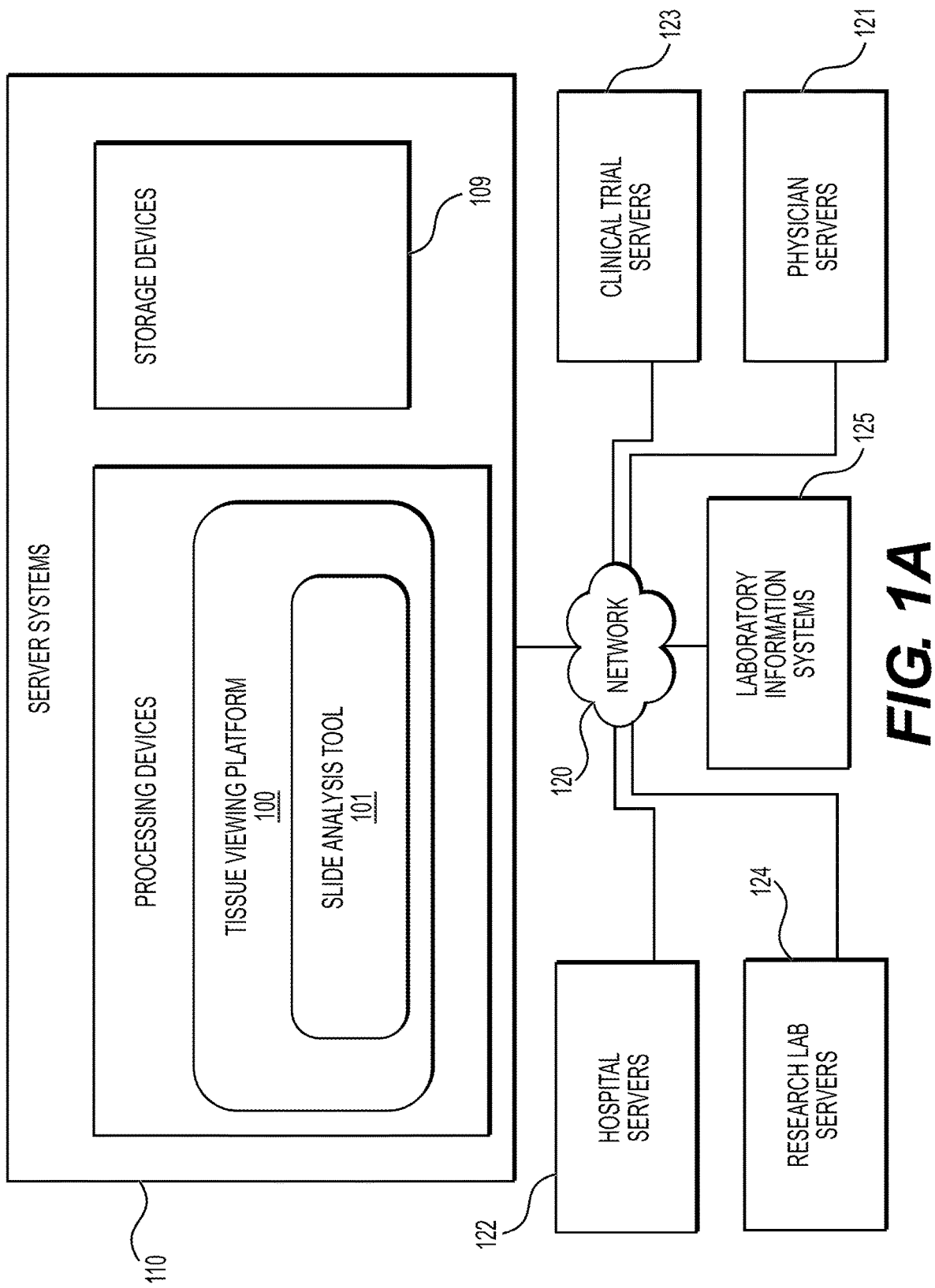
FIG. 1A illustrates an exemplary block diagram of a system and network for processing images, for example image matching, according to techniques presented herein.

According to certain aspects of the disclosure, methods and systems are disclosed for providing a system/process configured for matching digitized slides among patients (e.g., slide matching or image matching). Slide matching or image mapping may refer to providing an indication or percentage chance of whether two inputted medical digitized slides belong to the same individual. The methods and systems may utilize machine learning techniques as will be discussed in more detail below.

Pathology refers to the study of diseases. More specifically, pathology may refers to performing tests and analysis that are used to diagnose diseases. For example, tissue samples may be placed onto slides to be viewed under a microscope by a pathologist (e.g., a physician that is an expert at analyzing tissue samples to determine whether any abnormalities exist). That is, pathology specimens may be cut into multiple sections, stained, and prepared as slides for a pathologist to examine and render a diagnosis.

The process of using computers to assist pathologists is called computational pathology. Computing methods used for computational pathology may include, but are not limited to, statistical analysis, autonomous or machine learning, and artificial intelligence (AI). AI may include, but is not limited to, deep learning, neural networks, classifications, clustering, and regression algorithms. By using computational pathology, lives may be saved by helping pathologists improve their diagnostic accuracy, reliability, efficiency, and accessibility. For example, computational pathology may be used to assist with detecting whether slides correctly correspond to the same patient, thereby allowing pathologist to accurately diagnose patients.

Histopathology refers to the study of a specimen that has been placed onto a slide. For example, a digital pathology image may be comprised of a digitized image of a microscope slide containing the specimen (e.g., a smear). One method a pathologist may use to analyze an image on a slide is to identify nuclei and classify whether a nucleus is normal (e.g., benign) or abnormal (e.g., malignant). To assist pathologists in identifying and classifying nuclei, histological stains may be used to make cells visible. Many dye-based staining systems have been developed, including periodic acid-Schiff reaction, Masson's trichrome, Nissl and methylene blue, and Hematoxylin and Eosin (H&E).

A digitized image may be prepared to show a stained microscope slide, which may allow a pathologist to manually view the image on a slide and estimate a number of stained abnormal cells in the image. Computational processes using machine learning models and devices may be used to assist pathologists in detecting whether digitized images correspond to the correct individual. Using AI to verify that digitized slides belong to each respective recorded individual has the potential to improve patient care and lead to more accurate analyses.

As will be discussed in more detail below, computational pathology processes and devices of the present disclosure may provide an integrated platform allowing a fully automated process including data ingestion, processing and viewing of digital pathology images via a web-browser or other user interface, while integrating with a laboratory information system (LIS). Further, clinical information may be aggregated using cloud-based data analysis of patient data. The data may come from hospitals, clinics, field researchers, etc., and may be analyzed by machine learning, computer vision, natural language processing, and/or statistical algorithms to do real-time monitoring and forecasting of health patterns at multiple geographic specificity levels.

Within the field of pathology, it may be critical for a pathologist to have the correct information of one's patients in order to make a diagnosis. In particular, to illustrate one potentially catastrophic problem, data from one patient may be mixed in with the data from another patient. For instance, this may occur at the slide level, when a pathologist receives a plurality of whole slide images ("WSIs") that do not correspond to the same patient. It is possible that a pathologist may receive a set of WSIs that are supposed to belong to a single individual and one or more WSI may belong to a different individual. For example, the error may occur due to mistakes made during the scanning of individual specimens, or due to mistakes within a laboratory information system. If a pathologist analyses incorrect patient WSIs, this may lead to a misdiagnoses.

Every individual has unique DNA, which may be translated to mRNA, and then to proteins within a tissue sample. Each individual's tissues are essentially unique and therefore may be visually matched. An image of an individual's tissues (i.e., WSIs) may be identified and compared to other tissue images to determine if they match and thus correspond to the same individual.

As will be discussed in more detail below, in various embodiments, systems and methods are described for utilizing image processing techniques and/or machine learning to determine if one or more slides belongs to the same patient or not.

Further, in various embodiments, systems and methods are described for using various machine learning techniques in order to match patient slides. By training one or more slide matching AI models, e.g., via supervised, semi-supervised learning, or supervised learning to learn how to match WSI based on image characteristics, the trained slide matching AI models may be able to output whether any of the inputted slides do not match and correspond to a different individuals. There may be multiple ways to build a system, as described below.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a"

and "an" herein do not denote a limitation of quantity, but rather denote the presence of one or more of the referenced items.

Techniques presented herein describe patching and/or repairing local regions of blur using computer vision and/or machine learning to correct and/or increase the percentage of a medical image that can be considered in-focus without needing to rescan a specimen and/or subject.

Techniques presented herein may relate to using multiple scans of the same image and using image processing techniques and/or machine learning to combine them into one coherent, low-blur image, and/or using generative methods to fill in blur.

As used herein, a "machine learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine learning model is generally trained using training data, e.g., experiential data and/or samples of input data, which are fed into the model in order to establish, tune, or modify one or more aspects of the model, e.g., the weights, biases, criteria for forming classifications or clusters, or the like. Deep learning techniques may also be employed. Aspects of a machine learning model may operate on an input linearly, in parallel, via a network (e.g., a neural network), or via any suitable configuration.

The execution of the machine learning model may include deployment of one or more machine learning techniques, such as linear regression, logistical regression, random forest, gradient boosted machine (GBM), deep learning, and/or a deep neural network. Supervised and/or unsupervised training may be employed. For example, supervised learning may include providing training data and labels corresponding to the training data, e.g., as ground truth. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc.

FIG. 1A illustrates a block diagram of a system and network for processing images to produce a low blur image, using machine learning, according to an exemplary embodiment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present disclosure, the electronic network 120 may also be connected to server systems 110, which may include processing devices that are configured to implement a tissue viewing platform 100, which includes a slide analysis tool 201 for determining specimen property or image property information pertaining to digital pathology image(s), and using machine learning to classify a specimen, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the one or more storage devices 109. Server systems 110 may further include one or more machine learning tool(s) or capabilities. For example, the processing devices may include a machine learning tool for a tissue viewing platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in one of the laboratory information systems 125. However, the correct tissue classification information is not always paired with the image content. Additionally, even if a laboratory information system is used to access the specimen type for a digital pathology image, this label may be incorrect due to the face that many components of a laboratory information system may be manually input, leaving a large margin for error. According to an exemplary embodiment of the present disclosure, a specimen type may be identified without needing to access the laboratory information systems 125, or may be identified to possibly correct laboratory information systems 125. For example, a third party may be given anonymized access to the image content without the corresponding specimen type label stored in the laboratory information system. Additionally, access to laboratory information system content may be limited due to its sensitive content.

Figure 1B:
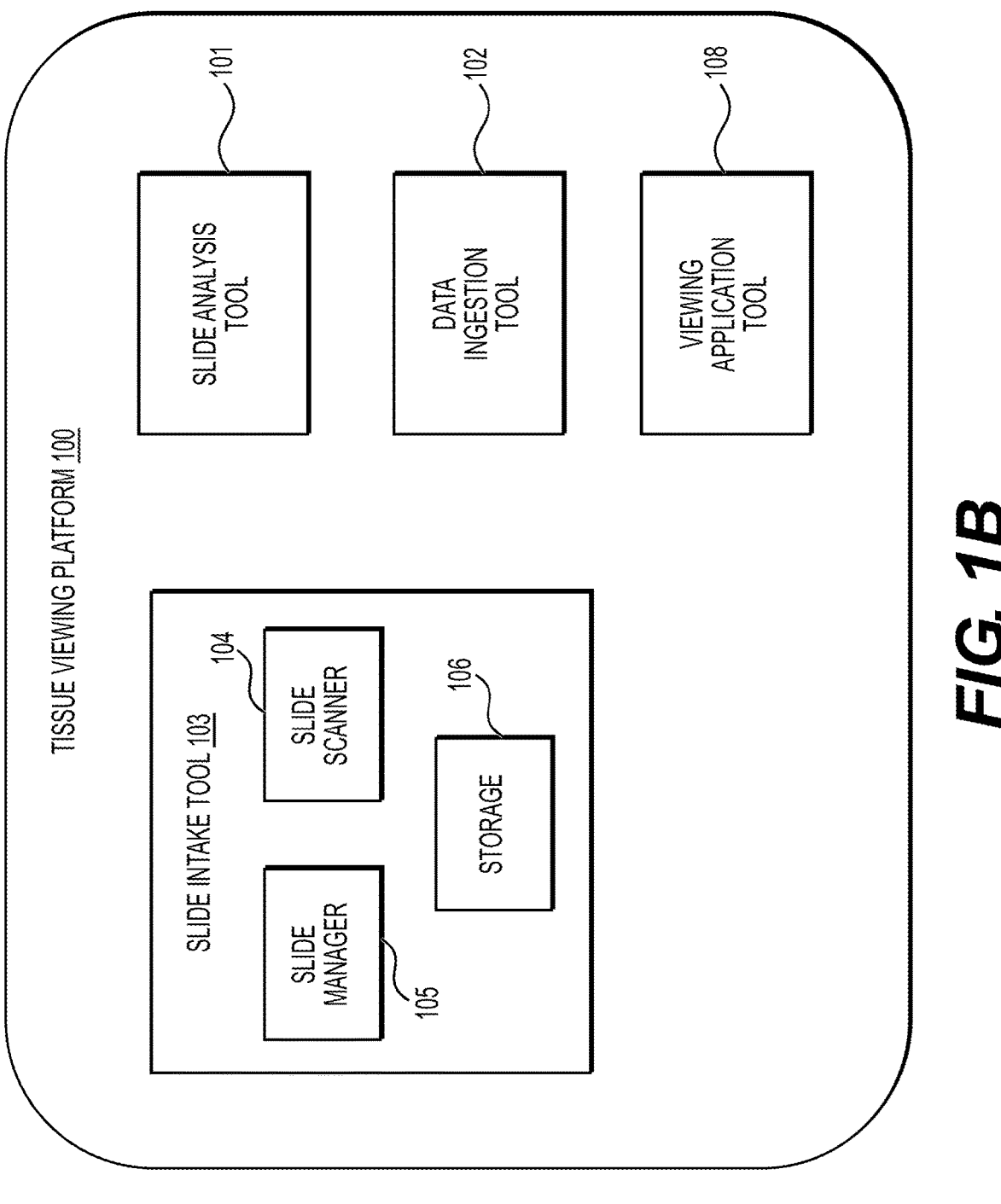
FIG. 1B illustrates an exemplary block diagram of a tissue viewing platform according to techniques presented herein.

FIG. 1B illustrates an exemplary block diagram of a tissue viewing platform 100 for determining specimen property of image property information pertaining to digital pathology image(s), using machine learning. For example, the tissue viewing platform 100 may include a slide analysis tool 101, a data ingestion tool 102, a slide intake tool 103, a slide scanner 104, a slide manager 105, a storage 106, and a viewing application tool 108.

The slide analysis tool 101, as described below, refers to a process and system for processing digital images associated with a tissue specimen, and using machine learning to analyze a slide, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., a pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, and each of its components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include one or more storage devices 109 for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools and modules may be located on a device that may be connected to an electronic network 120, such as the Internet or a cloud service provider, through one or more computers, servers, and/or handheld mobile devices.

Figure 1C:
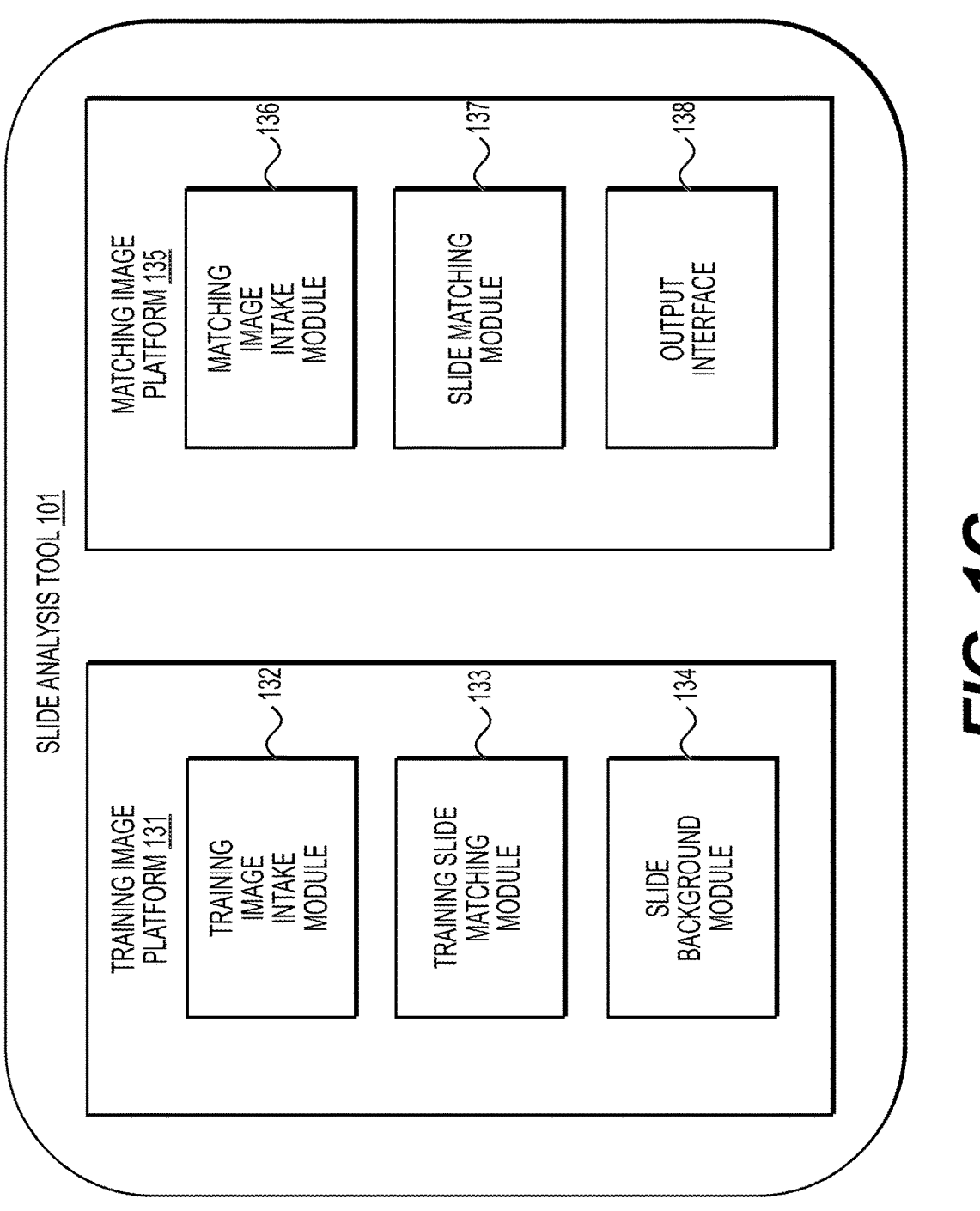
FIG. 1C illustrates an exemplary block diagram of a slide analysis tool, according to techniques presented herein.

FIG. 1C illustrates an exemplary block diagram of a slide analysis tool 201, according to an exemplary embodiment of the present disclosure. The slide analysis tool may include a training image platform 131 and/or a matching image platform 135.

The training image platform 131, according to one embodiment, may create or receive training images that are used to train a machine learning system to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized image samples from a 3D imaging device, such as micro-CT.

The training image intake module 132 may create or receive a dataset comprising one or more training images corresponding to either or both of images of a human tissue and images that are graphically rendered. For example, the training images may be received from any one or any combination of the server systems 110, physician servers 121, and/or laboratory information systems 125. This dataset may be kept on a digital storage device. The training slide matching module 133 may intake training data related to matching slides (e.g., WSIs) relating to the same individual or patient. For example, the training slide matching module 133 may intake full WSIs, or may intake one or more tiles of WSIs. The training slide matching module 133 may include the ability to break an inputted WSI into tiles to perform further analysis of individual tiles of a WSI. The training slide matching module 133 may utilize any binary classification, triplet loss, or embedding/vector of WSI (including using pairwise combinations or sequences) in order to help provide training for the machine learning techniques described herein. The slide background module 134 may analyze images of tissues and determine a background within a digital pathology image. It is useful to identify a background within a digital pathology slide to ensure tissue segments are not overlooked.

According to one embodiment, the matching image platform 135 may include a matching image intake module 136, a slide matching module 137, and an output interface 138. The matching image platform 135 may receive a plurality of electronic images and apply the machine learning model to the received plurality of electronic images to determine whether the plurality of electronic images match (e.g., correspond to the same individual). For example, the plurality of electronic images may be received from any one or any combination of the server systems 110, physician servers 121, hospital servers 122, clinical trial servers 123, research lab servers 124, and/or laboratory information systems 125. The matching image intake module 136 may receive WSI's corresponding to one or more patients/individuals. The slide matching module 137 may apply one or more machine learning models to a group of WSI in order to determine whether all WSIs correspond to the same patient. For example, the slide matching module 137 may apply the machine learning model to determine whether one or more WSIs correspond to the same patient. The slide matching module 137 may be capable of outputting an indication of whether two slides match. The indication may be a yes or no answer, a probability that the slides may match, a distance function corresponding to how similar to slides are (e.g., a Euclidean distance), or any alternative indicator of whether two slides match. When a distance function is outputted, two similar images may have a low Euclidean distance and two images that do not match may have a large Euclidean distance.

The output interface 138 may be used to output information about the inputted images and whether the images inputted belong to the same individual (e.g., to a screen, monitor, storage device, web browser, etc.). The output information may include information related to two specific slides that have been compared. For instance, the information may be whether two slides match or a probability that two slides match, or a distance function. In another embodiment, where a plurality of images are inputted into the matching image intake module 136, the output interface may be able to provide information of whether all inputted images match. Additionally, the output interface may indicate any images that do not match the majority of the plurality of images. This output may be an indicator that said images do not match or a probability of whether certain images under a threshold value do not match. Whether or not two images match be determined based on a distance function. In another embodiment, the matching image intake module 136 may receive a plurality of images for more than one individual with indicator as to which individual each slide/images belongs. In this embodiment, the output interface may indicate whether all slides correctly match to their respective indicated individual. This may be done as either yes/no or by a percentage chance that each slide belongs to a respective group.

Figure 2A:
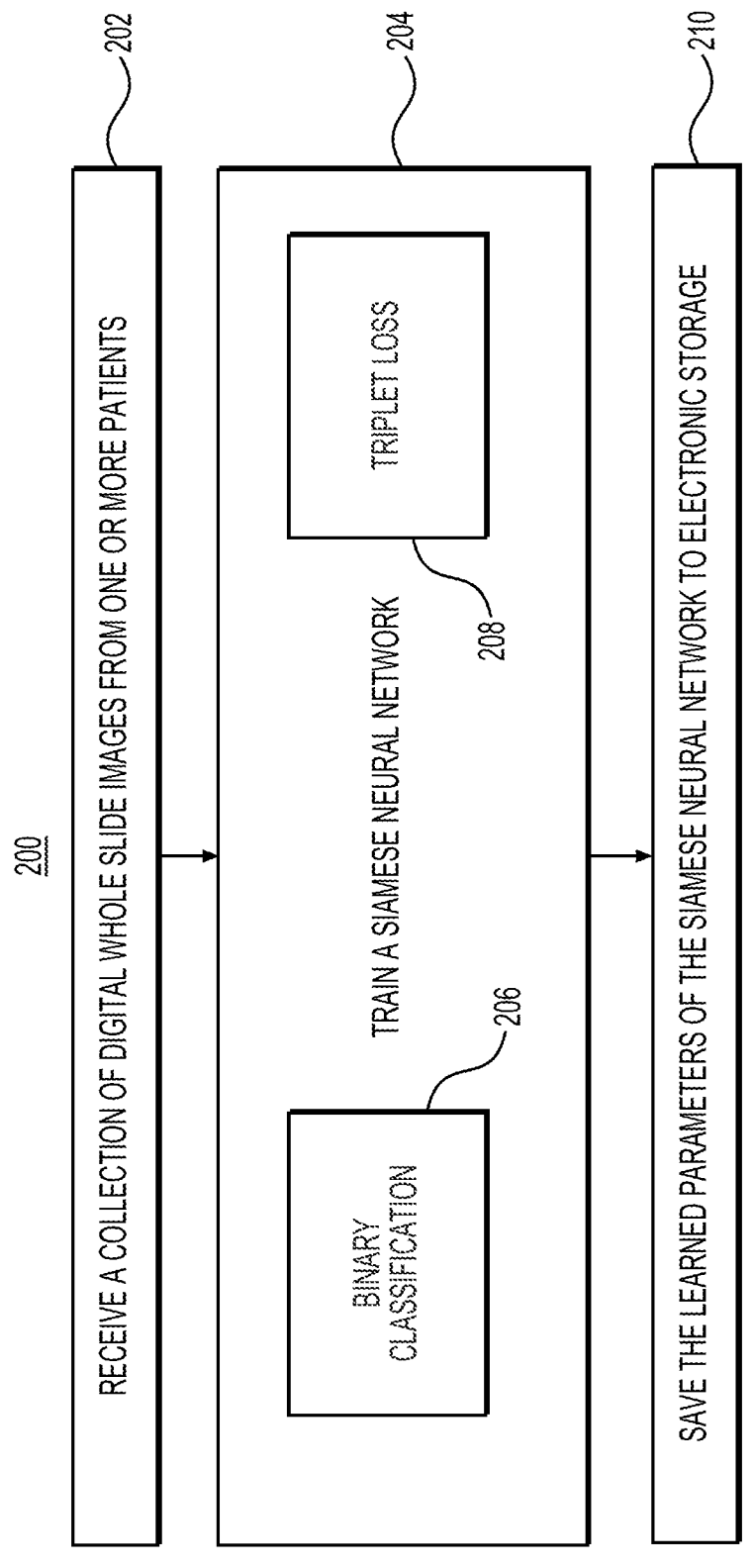
FIG. 2A is a flowchart illustrating how to train an algorithm for image matching, according to techniques presented herein.

FIG. 2A illustrates a flowchart illustrating how to train an algorithm for image matching, according to techniques presented herein. The flowchart 200 of FIG. 2A depicts steps that may be performed by, for example, training image platform 131 of slide analysis tool 101 as described above in FIG. 1C. Alternatively, the method 500 may be performed by an external system.

Flowchart 200 depicts example training steps to train a machine learning module as describe in further detail in steps 202, 204, and 210. The machine learning module may utilize pairwise combinations within a "Siamese" neural network as discussed further below.

At step 202, the system (e.g., the training image intake module 132 of slide analysis tool 101) may receive a collection of digital WSIs from patients into electronic storage, e.g., cloud, RAM, hard drive, etc. These WSIs may be collectively referred to as training data. The training data may include a label or data that associate each slide with a particular individual or reference number. Alternatively, the server systems 110 or Network 120 may record and store information as to which individual each WSI corresponds. The training data may be WSIs or broken tiles/image patches of WSIs.

At step 204, the system (e.g., the training slide matching module 137 of slide analysis tool 101) may train a machine learning model. In one embodiment, the machine learning model may be a Siamese neural network. The Siamese neural network may contain two or more subnetworks. The subnetworks may use the same weights (i.e., tied weights) for most of the network, with untied weights used at the top of the network for comparison. The update of parameters during training (e.g., weights or layers) may be the same across both sub-networks. This form of network may excel at tasks such as face verification and can thus be repurposed for analyzing whether patients slides match.

There may be multiple ways to train the Siamese network within the system. In a first embodiment, the system may be trained using binary classification techniques 206. When the system is trained utilizing binary classification, the Siamese network may first generate one or more sets of two WSIs using the training data from step 202. The system may generate sets of matching slides that correspond to the same patient ("matching sets") and sets of non-matching slides that correspond to different patients ("non-matching sets"). These matching and non-matching sets may then be used to train the Siamese network. To do this, the system may first sample a random value p between 0 and 1. If p>t, where t is a hyperparameter threshold, the system may create non-matching sets by randomly selecting two slides belonging to two different patients and setting the output label to 0 indicating that the pair does not match. Otherwise, the system may create matching sets by choosing two slides from the same patient and setting the output label set to 1 indicating that the pair matches. The system may create as many matching and non-matching image sets as necessary to train the Siamese network.

When the system begins training, the platform may insert a first WSI of a set into a first subnetwork and insert the second WSI of the same set into the second subnetwork. The initial set may be of either matching or non-matching images. During training, both matching and non-matching sets may be input into the system to further train the system.

The subnetworks may be convolutional neural networks, recurrent neural networks, transformer neural networks, fully connected neural networks, etc. Each subnetwork may be capable of receiving an entire WSI as input. In another embodiment, subnetworks may receive a WSI that is broken into tiles. The system (e.g., the training image platform 131) may include intermediate steps that break the WSI into labeled tiles and then the tile collection may be fed into one of the respective subnetworks of the Siamese network. As the system receives two images from each set, the system may be trained from a ground truth based on whether the two images are matching or non-matching. The network as a whole may be trained with any form of binary classification loss desired (e.g., binary cross entropy loss, hinge loss, etc.). The system may calculate the loss using the outputs from the first and second image. The network training may further include using gradient descent and/or backpropagation (e.g., utilizing backpropagation to calculate the grade of the model) while updating the weights of the machine learning model until the loss is sufficiently reduced to minimize error on the training data. The updated model may then be saved (e.g., within the server systems 110).

In a second embodiment, the Siamese network may be trained utilizing a triplet loss function 208. The objective of triplet loss training may be to have the system (e.g., training image platform 131) create triplets. A triplet may be a set of three images including an anchor image, a positive image, and a negative image as will be further discussed below. Similar to the binary classification training, the subnetworks may be capable of receiving, as input, entire WSI or tiles of WSIs. The triplet loss training may include the system first selecting an "anchor" image from the training data imported at step 202. The anchor image may be the reference input that may be compared to for matching purposes during training. Next, the training image platform 131 may find a positive example (another image from the same patient as the anchor image) and a negative example (different patient image than the anchor image). The system may create as many triplets as needed to train the machine learning model. The machine learning model may then be trained on the sets of triplets to minimize the distance between the anchor images and positive examples and maximize the distance between the anchor image and negative examples. The system may create a Euclidean distance function to help explain the loss. Alternatively, any other distance metric, such as a cosine distance may be utilized. During training, the distance between the anchor and positive image may be reduced to a minimum and the distance between the anchor and negative images may be increased. The machine learning model may be trained using gradient descent/backpropagation until the loss is sufficiently reduced to minimize error on the training data.

At step 210, the system may save the learned parameters to electronic storage (e.g., storage devices 109 or alternative electronic storage, e.g., cloud, RAM, hard drive, etc.). The parameters may include any updated weights or biases for the trained neural network.

FIG. 2B is a flowchart illustrating methods for how to process an image (e.g., slide matching a set of image), according to one or more exemplary embodiments herein. FIG. 2B may illustrate a method that utilized the trained neural network that was descried in FIG. 2A. The exemplary method 250 (e.g., steps 252-258) of FIG. 2B depicts steps that may be performed by, for example, Matching Image Platform 135 of slide analysis tool 101. These steps may be performed automatically or in response to a request from a user (e.g., physician, pathologist, etc.). Alternatively, the method described in flowchart/method 250 may be performed by any computer process system capable of receiving image inputs such as device 700 and capable of including or importing the Siamese network described in FIG. 2A.

At step 252, the system (e.g., the matching image intake module 136) may receive a plurality of electronic medical images associated with a medical sample of a patient/user/individual. The system may store the medical images into the storage device 109 or alternative electronic storage, e.g., cloud, RAM, hard drive, etc. The medical images may be WSIs. In another embodiment, the system may receive sets of tiles that combine to form WSIs. The plurality of electronic medical images may be images of a single slice of a single specimen. Alternatively, the plurality of medical images may be of multiple slices, but for a single specimen of a particular individual. In another embodiment, the plurality of medical images may be of multiple different specimen associated with a single individual.

In addition to inputted WSIs, the system may have the ability to receive historical electronic medical images. Historical electronic medical images may refer to any previous medical images (e.g., WSIs) of one or more specimen for an individual. The historical electronic medical image may be of the same slice of a specimen, a different slice of the same specimen, or of a slice of a different specimen in. For example, historical electronic medical images may be received from stored images of a previous trip to a hospital for an individual. These historical electronic medical images may be received from hospital servers 122, research lab servers 124, the laboratory information system 125, physician servers 121, clinical trial servers 123, or any external system containing past medical images of an individual.

In another embodiment, the plurality of medical images may be from more than one user. In this embodiment, the plurality of medical images may be marked to differentiate slides for different users. For example, the system may receive multiple sets of medical images belonging to different individuals. These images may be marked or include data indicating the individual associated with each medical image. In another embodiment, the system may be capable of importing past medical images for each patient/user with images inputted into the system. The system may import these past medical files from hospital servers 122, research lab servers 124, laboratory information systems 125, clinical trial servers 123, or physician servers 121, or any other external server that can provide medical images.

At step 254, the system, (e.g., the slide matching module 137 of slide analysis tool 101) may run the trained Siamese network (described in FIG. 2A) on every combination of two images for a single patient and record the responses of the neural network. For example, if the system receives as input of seven medical images for a single patient, the trained Siamese network may be run on all twenty-one combinations of the seven figures being compared with one another. By applying the trained Siamese network on two images, the system may output a distance (e.g., a Euclidean distance) where a low distance corresponds to matching images and a large distance corresponds to two non-matching images. The system may determine whether two images match based on the distance between the two images. The machine learning algorithm may have a threshold value referred to as the predetermined similarity threshold, wherein if the distance between two images is less than the predetermined similarity threshold value, then the system may determine that two images match. Alternatively, if the distance is greater than the predetermined similarity threshold value, the system may determine that two images do not match.

In another embodiment, the slide analysis tool 101 may import one or more previous slides (e.g., historical electronic medical images) from a patient to analyze during step 254 in addition to the inputted WSIs. The historical electronic medical images may be chosen when the system is able to find a previous patient with the same name and birthdate (or similar birthday). Alternatively, historical electronic medical images of a patient may be imported into the system from network 120. A user may be able to select whether to compare inputted WSIs to found historical electronic medical images. The user may be able to access when the previous historical medical images were received.

This embodiment may be utilized to verify that all inserted slides correspond to the correct individual (e.g., to confirm that the historical electronic medical images on file for an individual actually correspond to that individual). For example, if all inserted medical images match with one another, but they do not match with the historical electronic medical images the system may flag (e.g., flagging) the inputted WSIs and historical electronic medical image for manual review. In this embodiment, the system may keep track of the historical image during matching. If all pairs not involving the historical image match (e.g., have a distance under the predetermined similarity threshold value) and all combinations of inserted WSIs with the historical image or images don't match (e.g., have a distance above a predetermined similarity threshold value), the system may record the information and notify a user of the system that the inserted slides match one another, but not the historical electronic medical image or images. This embodiment may be utilized to keep track of patient's medical images over time and to catch potential errors in the past recording of historical electronic medical images or errors in the inputted WSIs.

At step 256, the system may receive, from the trained machine learning system, an output indicating whether each pair of the electronic medical images matches within the predetermined similarity threshold (e.g., the distance is under a threshold value). The system may output a notification that all slides match, a list of all matching and non-matching WSIs, or a list of all slides flagged as non-matches.

At step 258, optionally, the system may flag any slides that potentially do not belong to a particular patient. Flag or flagging a slide may include, but is not limited to, creating a list within the system or storing a value with each slides that corresponds to matching/nonmatching. Flagging may also encompass, outputting to a user (e.g., through the tissue viewing platform 100) a visual notification that any and or all slides do not match. This may allow for an external user to perform manual review of any inputted slides and any historical electronic medical images utilized. In another embodiment, flagging may include creating a list of any slides that do not match and output the list to a user (e.g., through the tissue viewing platform 100). Alternatively, the system may display and/or output all slides that do not match, and may allow for a second manual review to confirm whether the appropriate slides were inserted.

The system described herein (e.g., slide analysis tool 101) may include algorithms that analyze all matching and non-matching pairs to determine which slides correspond to the patient. The algorithms may occur at step 256 of method 250 or step 458 of method 450, as described in further detail below. The algorithm may be capable of determining, based on various combinations of matching and non-matching slides combined with total slides, what slides correspond with an individual and what slides do not correspond. Below are a few exemplary situations that the system may encounter.

In a first example, the system may receive seven images that are supposed to correspond to a single individual, wherein one of the seven images does not actually correspond to the individual. The system may then input all twenty-one different pairings of the seven slides into the trained neural network. If six of the slides correspond to a patient and one slide was incorrectly inserted, then of the twenty-one different pairings, fifteen pairs will cause the system to output a distance below a predetermined similarity threshold value indicating matches and six pairs (all pairings involving the incorrect slide) will output a distance above the predetermined similarity threshold value. The system may then be capable of determining which slide does not match, by determining that a single slide was involved in every pair that that outputted a distance above a similarity threshold value. The system may then store the information and then flag the incorrect slide to a user of the system.

In a second example, the system may receive seven images that are supposed to correspond to a single individual, wherein two of the seven images do not actually correspond to the individual. In this example, the two non-matching slides do not correspond to the same individual. The system may then input all twenty-one different pairings of the seven slides into trained neural network. The system may then output ten matching pairs and eleven non-matching pairs. The system may then be capable of determining that two of the non-corresponding individuals were involved in all non-matches and thus flag only those two pairs as incorrect pairs. The system may then store this information and flag the incorrect slides to a user of the system.

In a third example, the system may receive seven images that are supposed to correspond to a single individual, wherein two of the seven images do not actually correspond to the individual. In this example, the two non-matching slides do belong to the same individual. The system may then input all twenty-one different pairings of the seven slides into the trained neural network. The system may then output eleven matching pairs and ten non-matching pairs. The slide analysis tool may then determine that two of the non-corresponding individuals were involved in all non-matches, and thus flag only those two pairs as incorrect pairs. The algorithm may also recognize the two slides involved in all non-matches, matched with each other, meaning that the two incorrect slides correspond to the same individual. The system may then store this information (including that the two non-matching slides correspond to the same individual) and flag the incorrect slides to a user of the system.

In a fourth example, the system may receive seven images that are supposed to correspond to a single individual, wherein six images are newly inserted images from step 252 and one image is imported from the individual's medical file (e.g., from the laboratory information system 125). The imported image may be labeled as a correct image. In this example, all six of the inserted slides may correspond to the same incorrect individual (not the same individual as the historical electronic medical image). The system may then input all twenty-one different pairings of the seven slides into the trained neural network. The system may then output fifteen matching pairs and six non-matching pairs (based on the outputted distance value). In this scenario, the system may recognize that the non-matching pairs all correspond with the imported "correct image." The system may then store this information and flag that all imported slides do not correspond to the historical electronic medical image.

Figure 3:
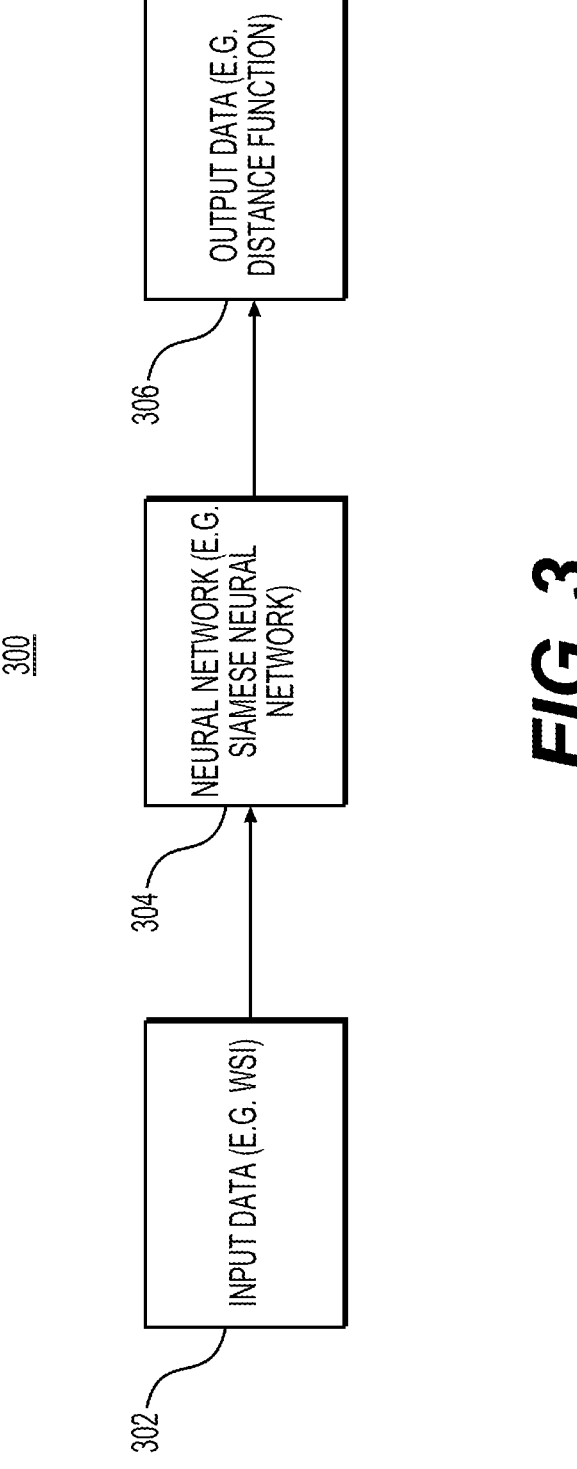
FIG. 3 illustrates a process matching one or more images, according to techniques presented herein.

FIG. 3 illustrates a process matching one or more images, according to techniques presented herein. In FIG. 3, input data 302 may be inserted into a trained neural network 304 (e.g., Siamese Neural Network). The input data 302 may correspond to the data described at step 252. The trained neural network 304 may correspond to the Siamese network trained based on flowchart 200 and utilized in step 254. Next, the neural network 304 may output data 306. The output data 306 may correspond to information on whether the input data "matches" (e.g., correspond to the same individual) as described in steps 254 and 256.

Figure 4A:
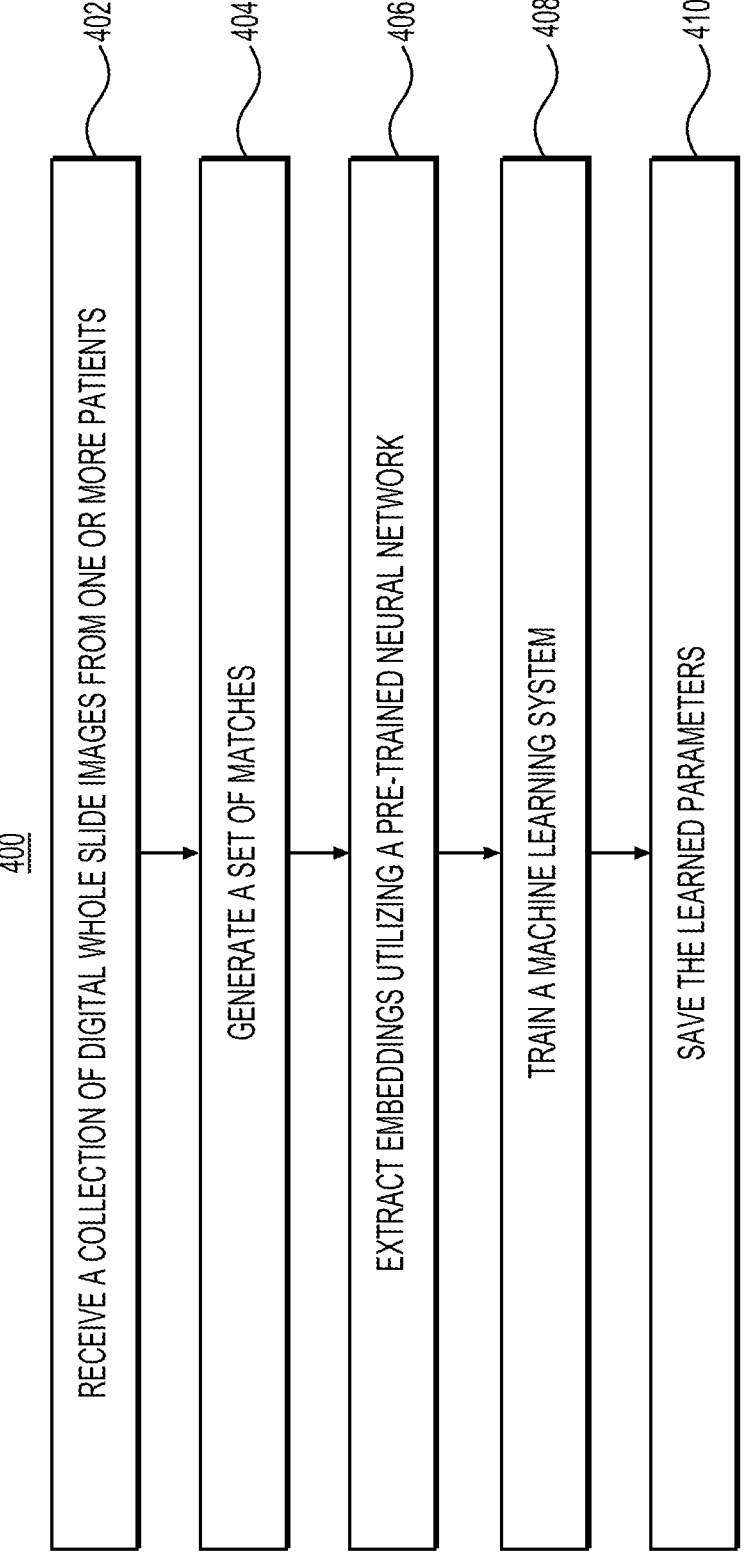
FIG. 4A is a flowchart illustrating how to train an algorithm for image matching, according to techniques presented herein.
Figure 4B:
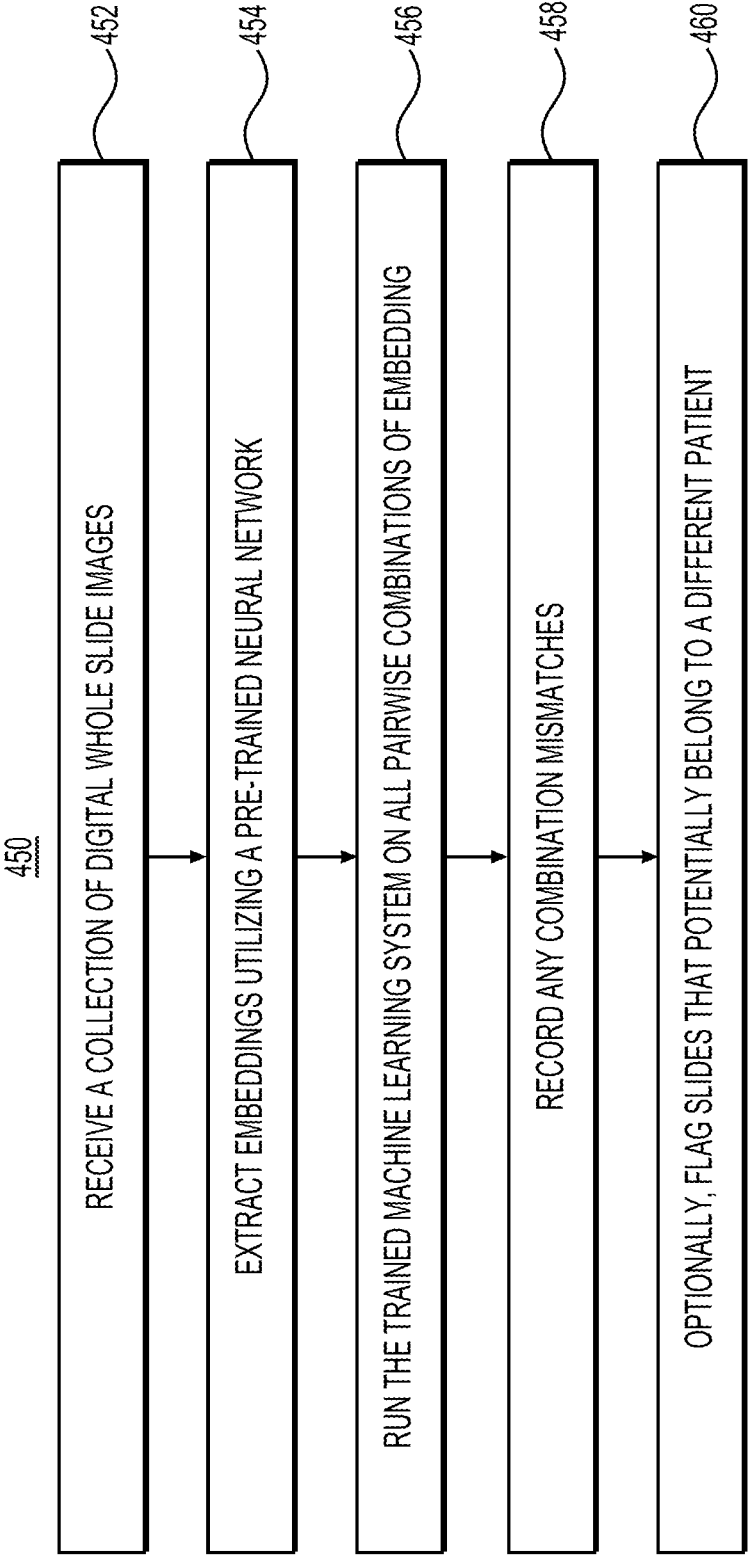
FIG. 4B is a flowchart illustrating methods for how to process an image (e.g., image matching), according to one or more exemplary embodiments herein.

FIG. 4A illustrates a flowchart illustrating how to train an algorithm for image matching, according to techniques presented herein The processes and techniques described in FIGS. 4A and 4B may contrast embeddings (e.g., vector representations of an image) to determine whether slides match. The method 400 of FIG. 4A depicts steps that may be performed by, for example, training image platform 131 of slide analysis tool 101 as described above in FIG. 1C. Alternatively, the method 500 may be performed by an external system.

Flowchart/method 400 depicts training steps to train a machine learning module as describe in further detail in steps 402-410. The machine learning module may utilize pairwise combination embeddings as discussed further below.

At step 402, the system (e.g., the training image intake module 132) may receive a collection of digital WSIs from patients into electronic storage, e.g., cloud, RAM, hard drive, etc. These WSIs may be collectively referred to as training data. The training data may include a label or data that associate each slide with a particular individual or reference number. Alternatively, the server systems 110 or network 120 may record and store information as to which individual each WSI corresponds. The training data may be WSIs or tiles/subportions of WSIs.

At step 404, the system (e.g., training slide matching module 133 of slide analysis tool 101), may generate a set of matches to utilize for training the machine learning model. The matches may be similar to the matches utilized for training in FIG. 2A step 204. For instance, the training slide matching module 133 may sample a random value p between 0 and 1. If p>t, where t is a hyperparameter threshold, then randomly pick two slides from two different patients and set the label to 0 indicating that the pair does not match; otherwise, choose two slides from the same patient and the output label set to 1 indicating that the pair matches. Step 404, may be repeated as many times as necessary to create an adequate amount of sets of pairs with which to conduct training.

At step 406, the system (e.g., training slide matching module 133 of slide analysis tool 101) may extract an embedding from every WSI within the training data. An image embedding may be a vector representation of said image that is capable of being compared with additional image embeddings. A pre-trained neural network within the slide analysis tool 101 may be utilized to extract embeddings from all training data sets created at step 404. This neural network may be referred to as the embedding machine learning module. In another embodiment, the embedding machine learning module may be located within training slide matching module 133. In another embodiment, the embedding machine learning module may be located externally from slide analysis tool 101 and accessed by the slide analysis tool 101 through network 120. The embedding machine learning module may be trained directly to do perform the task of extracting embeddings from images. The embedding machine learning module may be trained via supervised, unsupervised, or self-supervised. Next, once the embeddings are extracted for an image, the embeddings may be concatenated to form a single unified vector for each image of the training data.

At step 408, the system (e.g., the training slide matching module 133 of slide analysis tool 101) may train the machine learning module. The training may be conducted so that system may determine if each concatenated vector is from the same or a different patient, by utilizing labels that were ascribed at step 404. The training may be performed until a training error on the training data of step 402 is below a threshold value. This threshold value may be predetermined or determined by the system or system administrator. The machine learning module may be a fully connected network, a support vector machine, a nearest neighbor, a random forest, etc.

At step 410, the system may save the learned parameters to electronic storage (e.g., storage devices 109 or alternative electronic storage, cloud, RAM, hard drive, etc.). The parameters may include any updated weights or biases for the trained neural network.

FIG. 4B is a flowchart illustrating methods for how to process an image (e.g., image matching), according to one or more exemplary embodiments herein. FIG. 4B may illustrate a method that utilized the neural network that was trained in FIG. 4A. The exemplary method 450 (e.g., steps 452-458) of FIG. 4B depicts steps that may be performed by, for example, matching image platform 135 of slide analysis tool 101. These steps may be performed automatically or in response to a request from a user (e.g., physician, pathologist, etc.). Alternatively, the method described in flowchart 450 may be performed by any computer process system capable of receiving image inputs such as device 700 and capable of including or importing the neural network described in FIG. 4A.

At step 452, the system (e.g., the matching image intake module 136) may receive a plurality of electronic medical images associated with a medical sample of a patient/user/individual. The system may store the medical images into the storage device 109 or alternative electronic storage, e.g., cloud, RAM, hard drive, etc. The medical images may be WSIs. In another embodiment, the system may receive sets of tiles that combine to form WSIs. The plurality of electronic medical images may be images of a single slice of a single specimen. Alternatively, the plurality of medical images may be of multiple slices, but for a single specimen of a particular individual. In another embodiment, the plurality of medical images may be of multiple different specimen associated with a single individual.

In addition to inputted WSIs, the system may have the ability to receive historical electronic medical images. Historical electronic medical images may refer to any previous medical images (e.g., WSIs) of one or more specimens associated with an individual. The historical electronic medical image may be of the same slice of a specimen, a different slice of the same specimen, or of a slice of a different specimen. For example, historical electronic medical images may be received from stored images of a previous trip to a hospital for an individual. These historical electronic medical images may be received from hospital servers 122, research lab servers 124, the laboratory information system 125, physician servers 121, clinical trial servers 123, or any external system containing past medical images of an individual.

In another embodiment, the plurality of medical images may be from more than one user. In this embodiment, the plurality of medical images may be marked to differentiate slides for different users. For example, the system may receive multiple sets of medical images belonging to different individuals. These images may be marked or include data indicating which individual each medical image is supposed to belong to. In another embodiment, the system may be capable of importing past medical images for each patient/user with images inputted into the system. The system may import these past medical files from hospital servers 122, research lab servers 124, laboratory information systems 125, clinical trial servers 123, or physician servers 121, or any other external server that can provide medical images.

At step 454, the system (e.g., the slide matching module 137 of slide analysis tool 101) may extract the embeddings from all of the plurality of electronic images inserted into the system at step 452. The system may perform the extraction of the embeddings utilizing a pre-trained neural network similar to the neural network described at step 406 in training. The pre-trained neural network may be located within the slide analysis tool 101 and may be utilized to extract embeddings from inserted images (e.g., collection of digital WSIs) at step 452. This neural network may be referred to as the embedding machine learning module. In another embodiment, the embedding machine learning module may be located within slide matching module 137. In another embodiment, the embedding machine learning module may be located externally from slide analysis tool 101 and accessed by the slide analysis tool 101 through network 120. The embedding machine learning module may be trained directly to perform the task of extracting embeddings from images. The embedding machine learning module may be trained via supervised, unsupervised, or self-supervised techniques.

Once the embeddings are extracted for an image, the embeddings may be concatenated to form a single unified vector for each image. The unified vectors may capture all salient information related to an image within a single vector. These single unified vectors for each image may be stored via storage devices 109.

At step 456, the system, (e.g., the slide analysis tool 101 and more specifically slide matching module 137) may run the trained pairwise combination network (described in FIG. 4A) on every combination of two unified vectors (corresponding to inserted images at 452) for a single patient and record the responses of the neural network. For example, if the system receives, as input, seven medical images for a single patient, the trained pairwise combination network may be run on all twenty-one combinations of the seven concatenated embeddings being compared with one another. By applying the trained pairwise network on two images, the system may output a distance (e.g., a Euclidean distance) where a low distance corresponds to matching images and a large distance corresponds to two non-matching images. The system may determine whether two images match based on the distance between the two images. The machine learning may have a predetermined similarity threshold value, wherein if the distance between two images is less than the predetermined similarity threshold value, then the system determines two images mage. Alternatively, if the distance is greater than the predetermined similarity threshold value, the system may determine that two images do not match.

In another embodiment, the system (e.g., the slide analysis tool 101) may import one or more previous slides (e.g., a historical electronic medical image) from a patient to utilize during step 456. This embodiment may verify that all inserted slides do not match to a single incorrect individual, meaning the inserted slides match with one another, but not to the historical electronic medical image. Alternatively, this method may be used to verify that the historical electronic medical image is correctly associated with a current patient/individual. In this embodiment, the system may keep track of the historical image during matching. If all pairs not involving the historical image match (e.g., have a distance under the predetermined similarity threshold value) and all combination of inserted WSIs with the historical image do not match (e.g., have a distance above a predetermined similarity threshold value), the system may record the information and notify a user of the system.

At step 458, similar to step 256, the system may receive, from the trained machine learning system, an output indicating whether each pair of the electronic medical images matches within the predetermined similarity threshold (e.g., the distance is under a predetermined threshold value). The system may output a notification that all slides match, a list of all matching and non-matching WSIs, or a list of all slides flagged as non-matches.

At step 460, similar to step 258, optionally, the system may flag any slides that potentially do not belong to a particular patient. The slide system may include algorithms that analyze all matching and non-matching pairs to determine which slides correspond to the patient. The algorithm may be capable of determining, based on various combinations of matching and non-matching slides combined with total slides, what slides correspond with an individual and what slides do not correspond.

Figure 5A:
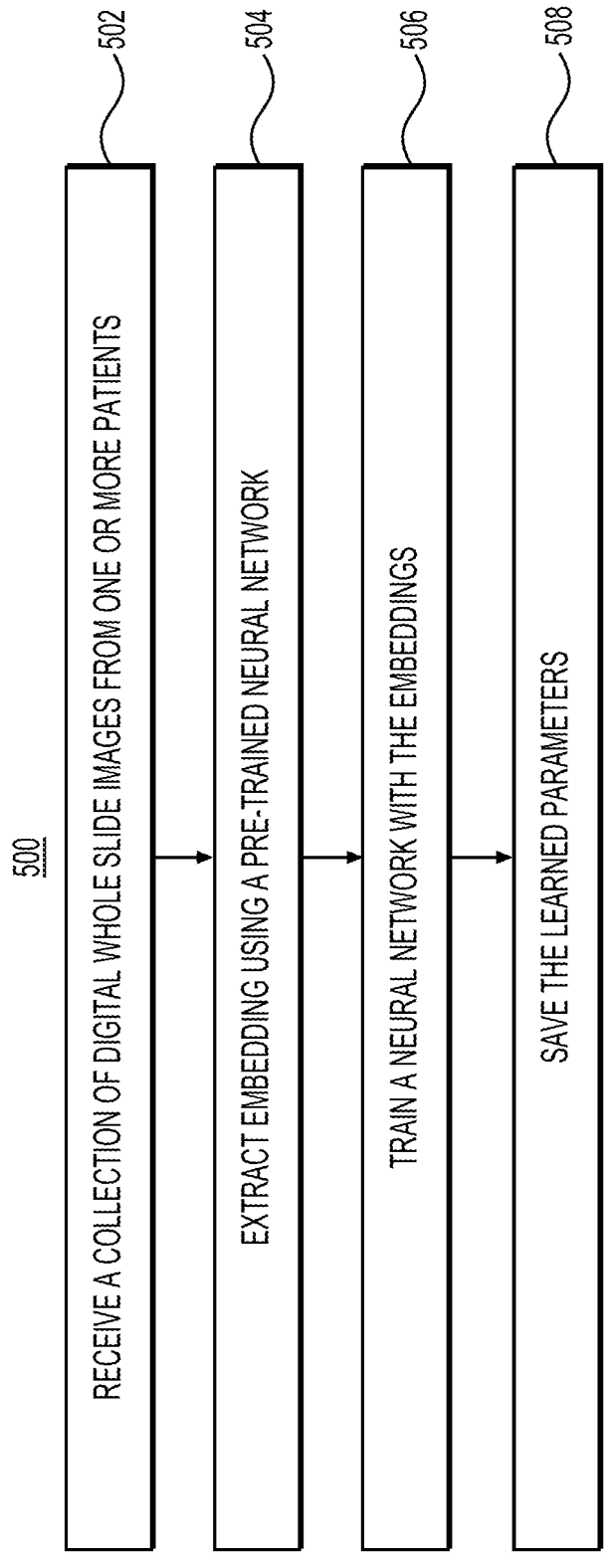
FIG. 5A is a flowchart illustrating methods to train an algorithm for image matching an image, according to techniques presented herein.

FIG. 5A illustrates a flowchart for training an algorithm for image matching, according to techniques presented herein. The method 500 of FIG. 5A depicts steps that may be performed by, for example, training image platform 131 of slide analysis tool 101 as described above in FIG. 1C. Alternatively, the method 500 may be performed by an external system.

Flowchart/method 500 depicts training steps to train a machine learning module as described in further detail in steps 502-508. The machine learning module may utilize data sequences (e.g., embedding) as discussed further below. By utilizing data sequences (e.g., embedding), the machine learning module may be capable of receiving as input a variable number of inputs (e.g., embedding), rather than a fixed size input such as a single vector. Further, the input data may be fed to the machine learning module simultaneously and might not necessarily have any sequential ordering related to input data.

At step 502, the system (e.g., the training image intake module 132) may receive a collection of digital WSIs from patients into electronic storage, e.g., cloud, RAM, hard drive, etc. These WSIs may be collectively referred to as training data. The training data may include a label or data that associate each slide with a particular individual or reference number. Alternatively, the server systems 110 or Network 120 may record and store information as to which individual each WSI corresponds to. The training data may be WSIs or broken tiles of WSIs.

At step 504, the system (e.g., the training slide matching module 133 of slide analysis tool 101) may extract embedding from all training data. An image embedding may be a vector representation of said image that is capable of being compared with additional image embeddings. A pre-trained neural network within the system may be utilized to extract embeddings from all training data sets created at step 404. This neural network may be referred to as the embedding machine learning module. In another embodiment, the embedding machine learning module may be located externally from slide analysis tool 101 and accessed by the slide analysis tool 101 through network 120. The embedding machine learning module may be trained directly to perform the task of extracting embeddings from images. The embedding machine learning module may be trained via supervised, unsupervised, or self-supervised techniques. Next, once the embeddings are extracted for an image, the embeddings may be concatenated to form a single unified vector for each image.

At step 506, the system (e.g., the training slide matching module 133 of slide analysis tool 101) may train a neural network with the embeddings that can handle "sequence" data, e.g., a recurrent neural network, transformer, 1-D convolutional neural network using the embeddings from each slide in the training data as input. Handling "sequence" data may refer to the ability of the system to receive as input a variable number of embeddings/vectors. During training, the neural network may, with probability p, randomly swap one of the embeddings with another embedding from a different patient. After swapping embeddings, the output label for the sequence may be set to 0 to indicate a mismatch, otherwise it is set to 1 to indicate they are all matches. The output may be any desired output for binary classification, for example hinge loss, binary cross entropy loss, etc.

At step 508, the system may save the learned parameters to electronic storage (e.g., storage devices 109 or alternative electronic storage, cloud, RAM, hard drive, etc.). The parameters may include any updated weights or biases for the trained neural network.

Figure 5B:
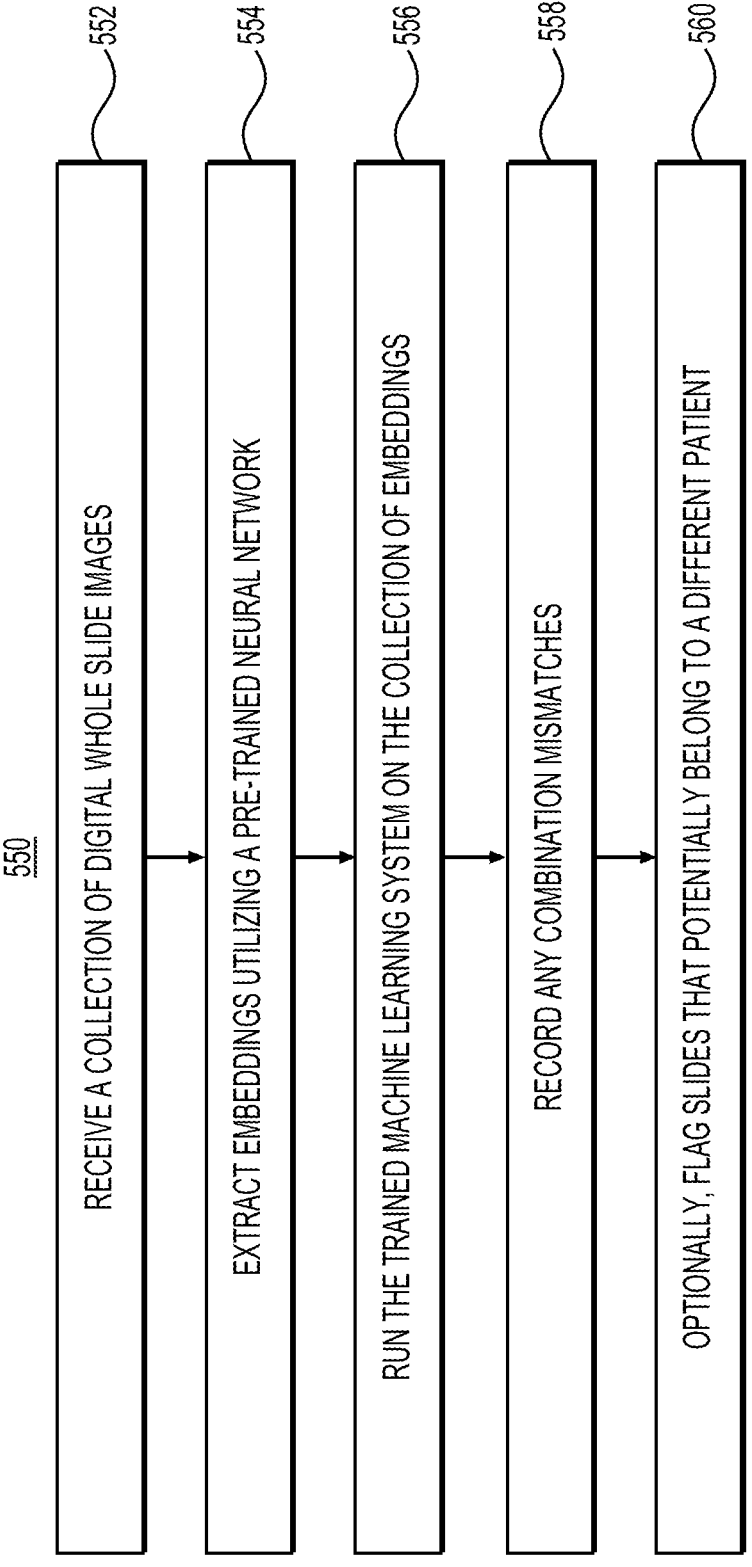
FIG. 5B is a flowchart illustrating methods for how to process an image (e.g., image matching), according to one or more exemplary embodiments herein.

FIG. 5B is a flowchart illustrating methods for how to process an image (e.g., image matching), according to one or more exemplary embodiments herein. FIG. 5B may illustrate a method that utilizes the neural network that was trained in FIG. 5A. The exemplary method 550 (e.g., steps 552-560) of FIG. 5B depicts steps that may be performed by, for example matching image platform 135 of slide analysis tool 101. These steps may be performed automatically or in response to a request from a user (e.g., physician, pathologist, etc.). Alternatively, the method described in flowchart 550 may be performed by any computer processor capable of receiving image inputs such as device 700 and capable of including or importing the neural network described in FIG. 5A.

At step 552, the system (e.g., the matching image intake module 136) may receive a plurality of electronic medical images associated with a medical sample of a patient/user/individual. The system may store the medical images into the storage device 109 or alternative electronic storage, for example in the cloud, RAM, hard drive, etc. The medical images may be WSIs. In another embodiment, the system may receive sets of tiles that combine to form WSIs. The plurality of electronic medical images may be images of a single slice of a single specimen. Alternatively, the plurality of medical images may be of multiple slices, but for a single specimen of a particular individual. In another embodiment, the plurality of medical images may be of multiple different specimen associated with a single individual.

In addition to inputted WSIs, the system may have the ability to receive historical electronic medical images. Historical electronic medical images may refer to any previous medical images (e.g., WSIs) of one or more specimen for an individual. The historical electronic medical image may be of the same slice of a specimen, a different slice of the same specimen, or of a slice of a different specimen in. For example, historical electronic medical images may be received from stored images of a previous trip to a hospital for an individual. These historical electronic medical images may be received from hospital servers 122, research lab servers 124, the laboratory information system 125, physician servers 121, clinical trial servers 123, or any external system containing past medical images of an individual.

In another embodiment, the plurality of medical images may be from more than one user. In this embodiment, the plurality of medical images may be marked to differentiate slides for different users. For example, the system may receive multiple sets of medical images belonging to different individuals. These images may be marked or include data indicating which individual each medical image is supposed to belong to. In another embodiment, the system may be capable of importing past medical images for each patient/user with images inputted into the system. The system may import these past medical files from hospital servers 122, research lab servers 124, laboratory information systems 125, clinical trial servers 123, or physician servers 121, or any other external server that can provide medical images.

At step 554, the system (e.g., the slide matching module 137 of slide analysis tool 101) may extract the embeddings from all of the plurality of electronic images inserted into the system at step 552. The system may perform the extraction of the embeddings utilizing a pre-trained neural network similar to the neural network described at step 506 in training. The pre-trained neural network may be located within the slide analysis tool 101 and may be utilized to extract embeddings from inserted images from step 552. This neural network may be referred to as the embedding machine learning module. In another embodiment, the embedding machine learning module may be located externally from slide analysis tool 101 and accessed by the slide analysis tool 101 through network 120. The embedding machine learning module may be trained directly to do perform the task of extracting embeddings from images. The embedding machine learning module may be trained via supervised, unsupervised, or self-supervised.

Once the embeddings are extracted for an image, the embeddings may be concatenated to form a single unified vector for each image. These single unified vectors for each image may be stored via storage devices 109.

At step 556, the system (e.g., the slide matching module 137 of slide analysis tool 101) may run the trained machine learning system described in step 506 on the collections of embeddings from step 554. By entering the collection of embeddings in the trained machine learning system, the system may then determine whether any of the inputted embeddings correspond to non-matching slides. For example, the system may provide a binary output that indicates whether all slides match or not.

At step 558, similar to step 256 and step 458, the system may receive, from the trained machine learning system, an output indicating whether each pair of the electronic medical images match within a predetermined similarity threshold (e.g., the distance is under a threshold value).

At step 560, similar to step 258 and step 460, optionally, the system may flag any slides that potentially do not belong to a particular patient. This may include, the system may displaying and or outputting all slides that do not match. Based on the flagging, this may then allow for a second manual review to confirm whether the appropriate slides were inserted.

FIG. 6 is a flowchart illustrating methods for how to process an image (e.g., image matching), according to one or more exemplary embodiments herein. Flowchart 600 may depicts steps to utilize a trained machine learning module as describe in further detail in steps 602-608.

At step 602, the system (e.g., the matching image intake module 136) may receive a plurality of electronic medical images associated with a medical sample of a patient.

At step 604, the system (e.g., the slide matching module 137) may provide the plurality of electronic medical images to a trained machine learning system, the trained machine learning system being trained to compare each of the plurality of electronic medical images to each other to determine whether each pair of the electronic medical images matches within a predetermined similarity threshold.

At step 606, the system (e.g., the slide matching module 137) may receive, from the trained machine learning system, an output indicating whether each pair of the electronic medical images matches within a predetermined similarity threshold.

At step 608, the system (e.g., the output interface 138) may output and/or store the output indicating whether each pair of the electronic medical images matches within a predetermined similarity threshold.

In one embodiment of the systems and methods described herein, the system may be capable of automatically identifying Laboratory Information System errors. After the system is trained, the system may be run on all slides associated with a particular patient. If the system determines that any slides do not match and correspond to a patient, a technician may be flagged to do a manual review to confirm that an error has not taken place.

In another embodiment of the systems and methods described herein, the system may be capable of comparing inserted medicals slides to the historical data of a patient or individual. It may be common for patients to have medical specimen taken multiples times while addressing a medial issue (e.g., medical specimen collected at an initial visit and again at a 6-month follow-up visit). An issue that may occur, is that the medical specimen or the WSI's of the medical specimen may be recorded during each visit as relating to distinct patients. This may occur in cases where a patient was originally seen at one hospital and then seen later at another hospital. This embodiment of the system may be used to verify and match patients WSI's over time despite recording errors or patient data being stored in distinct databases. To verify that WSI's for an individual match, the trained machine learning system may be fed the slide images from a patient along with slide images from past patients who may be the same individual (e.g., patients with the same birth date or a very similar name). If the machine learning system indicates that they are the same patient, the slides may be manually reviewed to determine if they correspond to the same patient or not.

Figure 7:
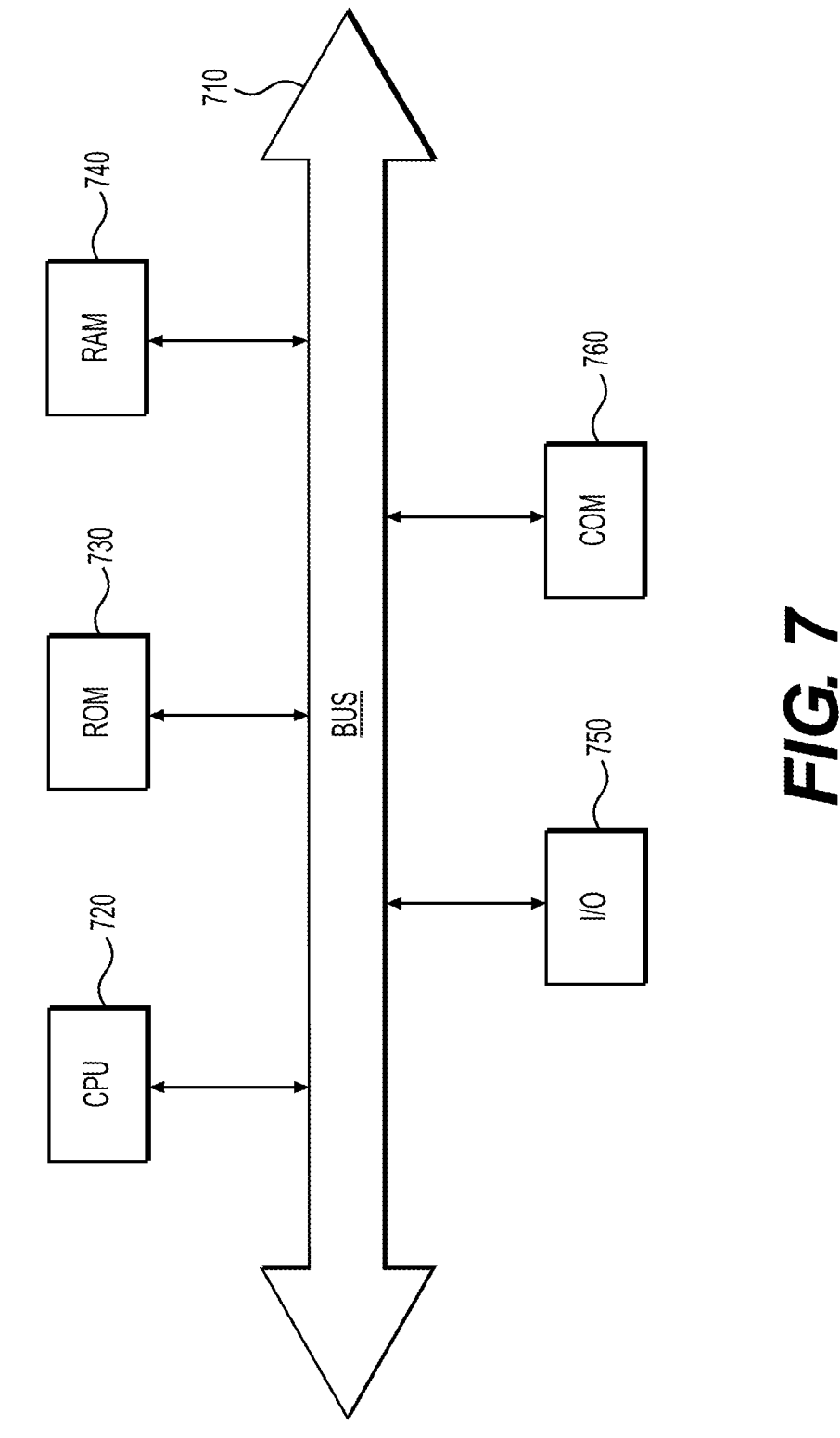
FIG. 7 depicts an example of a computing device that may execute techniques presented herein, according to one or more embodiments.

As shown in FIG. 7, device 700 may include a central processing unit (CPU) 720. CPU 720 may be any type of processor device including, for example, any type of special purpose or a general-purpose microprocessor device. As will be appreciated by persons skilled in the relevant art, CPU 720 also may be a single processor in a multi-core/multiprocessor system, such system operating alone, or in a cluster of computing devices operating in a cluster or server farm. CPU 720 may be connected to a data communication infrastructure 710, for example a bus, message queue, network, or multi-core message-passing scheme.

Device 700 may also include a main memory 740, for example, random access memory (RAM), and also may include a secondary memory 730. Secondary memory 730, for example a read-only memory (ROM), may be, for example, a hard disk drive or a removable storage drive.

Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 730 may include similar means for allowing computer programs or other instructions to be loaded into device 700. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical or other signals capable of being received by communications interface 760. These signals may be provided to communications interface 760 via a communications path of device 700, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 700 may also include input and output ports 750 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "read-able medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples to be considered as exemplary only.

What is claimed is:

1. A computer-implemented method for processing electronic medical images, comprising:
   receiving a plurality of electronic medical images associated with a medical sample of a first patient;
   providing the plurality of electronic medical images to a trained machine learning system, the trained machine learning system being trained with vectors extracted from each of the plurality of electronic medical images, the vectors concatenated to form unified vectors for each of the plurality of electronic medical images, wherein the trained machine learning system compares each of the plurality of electronic medical images to each other to determine whether each pair of the electronic medical images matches within a predetermined similarity threshold based on the training;
   receiving, from the trained machine learning system, an output indicating whether each pair of the plurality of electronic medical images matches within the predetermined similarity threshold, wherein a match within the predetermined similarity threshold indicates that a pair of electronic medical images is associated with the medical sample of the first patient; and
   outputting and/or storing the output indicating whether each pair of the electronic medical images matches within the predetermined similarity threshold.

2. The method of claim 1, wherein providing the plurality of electronic medical images to a trained machine learning system further comprises:
   determining one or more vectors associated with each of the plurality of electronic medical images; and
   providing the one or more vectors associated with each of the plurality of electronic medical images to the trained machine learning system.

3. The method of claim 1, wherein training of the trained machine learning system comprises:
   generating sets of matching and non-matching slides as training data; and
   training the machine learning system utilizing binary classification loss.

4. The method of claim 1, wherein training of the trained machine learning system comprises:
   generating sets of training data wherein each set included an anchor image, positive image, and negative image; and
   training the machine learning system utilizing triplet loss training techniques.

5. The method of claim 1, wherein training of the trained machine learning system comprises:
   generating sets of matching and non-matching slides as training data;
   extracting vectors from each of the plurality of electronic medical images;
   concatenating the vectors from each of the plurality of electronic medical images to form unified vectors for each image; and
   training the machine learning system utilizing pairwise neural network classifications.

6. The method of claim 1, wherein providing the plurality of electronic medical images to the trained machine learning system further comprises:

receiving a plurality of historical electronic medical images corresponding to one or more individuals.

7. The method of claim 1, wherein outputting and/or storing the output indicating whether each pair of the electronic medical images matches within the predetermined similarity threshold further comprises:

flagging any medical image outside of the predetermined similarity threshold for a human technician to perform review.

8. A system for processing electronic digital medical images, the system comprising:

at least one memory storing instructions; and at least one processor configured to execute the instructions to perform operations comprising:

receiving a plurality of electronic medical images associated with a medical sample of a first patient;

providing the plurality of electronic medical images to a trained machine learning system, the trained machine learning system being trained with vectors extracted from each of the plurality of electronic medical images, the vectors concatenated to form unified vectors for each of the plurality of electronic medical images, wherein the trained machine learning system compares each of the plurality of electronic medical images to each other to determine whether each pair of the electronic medical images matches within a predetermined similarity threshold based on the training;

receiving, from the trained machine learning system, an output indicating whether each pair of the plurality of electronic medical images matches within the predetermined similarity threshold, wherein a match within the predetermined similarity threshold indicates that a pair of electronic medical images is associated with the medical sample of the first patient; and outputting and/or storing the output indicating whether each pair of the electronic medical images matches within the predetermined similarity threshold.

9. The system of claim 8, wherein providing the plurality of electronic medical images to the trained machine learning system further comprises:

determining one or more vectors associated with each of the plurality of electronic medical images; and providing the one or more vectors associated with each of the plurality of electronic medical images to the trained machine learning system.

10. The system of claim 8, wherein training of the trained machine learning system comprises:

generating sets of matching and non-matching slides as training data; and training the machine learning system utilizing binary classification loss.

11. The system of claim 8, wherein training of the trained machine learning system comprises:

generating sets of training data wherein each set included an anchor image, positive image, and negative image; and training the machine learning system utilizing triplet loss training techniques.

12. The system of claim 8, wherein training of the trained machine learning system comprises:

generating sets of matching and non-matching slides as training data;

extracting vectors from each of the plurality of electronic medical images;

concatenating the vectors from each of the plurality of electronic medical images to form unified vectors for each image; and training the machine learning system utilizing pairwise neural network classifications.

13. The system of claim 8, wherein providing the plurality of electronic medical images to the trained machine learning system further comprises:

receiving a plurality of historical electronic medical images corresponding to one or more individuals.

14. The system of claim 8, wherein outputting and/or storing the output indicating whether each pair of the electronic medical images matches within the predetermined similarity threshold further comprises:

flagging any medical image outside of the predetermined similarity threshold for a human technician to perform review.

15. A non-transitory computer-readable medium storing instructions that, when executed by a processor, perform operations processing electronic digital medical images, the operations comprising:

receiving a plurality of electronic medical images associated with a medical sample of a first patient;

providing the plurality of electronic medical images to a trained machine learning system, the trained machine learning system being trained with vectors extracted from each of the plurality of electronic medical images, the vectors concatenated to form unified vectors for each of the plurality of electronic medical images, wherein the trained machine learning system compares each of the plurality of electronic medical images to each other to determine whether each pair of the electronic medical images matches within a predetermined similarity threshold based on the training;

receiving, from the trained machine learning system, an output indicating whether each pair of the plurality of electronic medical images matches within the predetermined similarity threshold, wherein a match within the predetermined similarity threshold indicates that a pair of electronic medical images is associated with the medical sample of the first patient; and outputting and/or storing the output indicating whether each pair of the electronic medical images matches within the predetermined similarity threshold.

16. The computer-readable medium of claim 15, wherein providing the plurality of electronic medical images to the trained machine learning system further comprises:

determining one or more vectors associated with each of the plurality of electronic medical images; and providing the one or more vectors associated with each of the plurality of electronic medical images to the trained machine learning system.

17. The computer-readable medium of claim 15, wherein providing the plurality of electronic medical images to the trained machine learning system further comprises:

receiving a plurality of historical electronic medical images corresponding to one or more individuals.

18. The computer-readable medium of claim 15, wherein outputting and/or storing the output indicating whether each pair of the electronic medical images matches within the predetermined similarity threshold further comprises:

flagging any medical image outside of the predetermined similarity threshold for a human technician to perform review.

* * * * *